US00PP11661P

United States Patent [19]

van Rijn

[11] Patent Number: Plant 11,661

[45] Date of Patent: Nov. 28, 2000

[54] ANTHURIUM PLANT NAMED 'LADY LOVE'

[75] Inventor: Leonardus van Rijn, Schipluiden, Netherlands

[73] Assignee: RijnPlant, Schipluiden, Netherlands

[21] Appl. No.: 09/291,093

[22] Filed: Apr. 14, 1999

[51] Int. Cl.[7] ..... A01H 5/00

[52] U.S. Cl. ..... Plt./365

[58] Field of Search ..... Plt./367, 365

*Primary Examiner*—Howard J. Locker
*Assistant Examiner*—Anne Marie Grünberg
*Attorney, Agent, or Firm*—C. A. Whealy

[57] ABSTRACT

A distinct cultivar of Anthurium plant named 'Lady Love', characterized by its upright plant habit; freely clumping growth habit; durable dark green leaves that are ovate in shape; numerous inflorescences that are positioned upright and beyond the foliage on strong and erect scapes; durable, glossy pink spathes with green lobes; year-round continuous flowering; and good post-production longevity.

1 Drawing Sheet

BACKGROUND OF THE INVENTION

The present invention relates to a new and distinct cultivar of Anthurium plant, botanically known as *Anthurium andreanum,* and hereinafter referred to by the cultivar name 'Lady Love'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor in July, 1994 of the Inventor's proprietary *Anthurium andreanum* selection code number 92-4 as the female, or seed, parent with the Inventor's proprietary *Anthurium andreanum* selection code number 94-13 as the male, or pollen, parent. The cultivar Lady Love was discovered and selected by the Inventor as a plant within the progeny of the stated cross in a controlled environment in Schipluiden, The Netherlands in August, 1996.

Asexual propagation of the new cultivar by tissue culture has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Lady Love'. These characteristics in combination distinguish 'Lady Love' as a new and distinct cultivar:

1. Upright plant habit.
2. Freely clumping growth habit.
3. Durable dark green leaves that are ovate in shape.
4. Numerous inflorescences that are positioned upright and beyond the foliage on strong and erect scapes.
5. Durable, glossy pink spathes with green lobes.
6. Year-round continuous flowering.
7. Good post-production longevity.

The new Anthurium can be compared to the female parent, the Inventor's proprietary selection code number 92-4. In side-by-side comparisons conducted by the Inventor in Schipluiden, The Netherlands, plants of the new Anthurium differ from plants of selection code number 92-4 in the following characteristics:

1. Plants of the new Anthurium are more compact than plants of the selection code number 92-4.
2. Plants of the new Anthurium have smaller and more durable leaves than plants of the selection code number 92-4.
3. Plants of the new Anthurium have pink-colored spathes whereas plants of the selection code number 92-4 have red-colored spathes.

The new Anthurium can be compared to the male parent, the Inventor's proprietary selection code number 94-13. In side-by-side comparisons conducted by the Inventor in Schipluiden, The Netherlands, plants of the new Anthurium differ from plants of selection code number 94-13 in the following characteristics:

1. Plants of the new Anthurium have smaller leaves than plants of the selection code number 94-13.
2. Plants of the new Anthurium have pink-colored spathes whereas plants of the selection code number 94-13 have red-colored spathes.
3. Plants of the new Anthurium and plants of the selection code number 94-13 differ in spathe shape.

The new Anthurium can be compared to the Anthurium cultivar 'Champion', disclosed in U.S. Plant Pat. No. 9,088. In side-by-side comparisons conducted by the Inventor in Schipluiden, The Netherlands, plants of the new Anthurium differ from plants of the cultivar 'Champion' in the following characteristics:

1. Plants of the new Anthurium grow faster than plants of the cultivar 'Champion'.
2. Plants of the new Anthurium are more freely clumping than plants of the cultivar 'Champion'.
3. Plants of the new Anthurium have rougher leaves than plants of the cultivar Champion.
4. Plants of the new Anthurium and of the cultivar 'Champion' differ in spathe color.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph sheet comprises a side perspective view of a typical potted plant of the cultivar 'Lady Love'. Leaf, spathe and spadix color in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe ten-month old plants grown in 14-cm containers in Schipluiden, The Netherlands, in a glass greenhouse with an average day temperature of 25° C. and an average night temperature of 19° C.

Botanical classification: *Anthurium andreanum* cultivar 'Lady Love'.

Parentage:

*Female parent.*—Inventor's proprietary *Anthurium andreanum* selection code number 92-4.

*Male parent.*—Inventor's proprietary *Anthurium andreanum* selection code number 94-13.

Propagation:

*Method.*—Typically by tissue culture.

*Time to initiate roots from a tissue culture propagule.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Freely clumping, bushy and dense, about five to seven shoots per plant. Appropriate for 12 to 20-cm containers.

*Plant height.*—About 25 to 28 cm from soil level to apex of spathes.

*Plant width.*—About 30 cm.

*Plant vigor.*—High.

*Growth rate.*—Rapid.

*Crop time.*—About 6 and 12 months are usually required from planting of young plants to finished plants in 12 and 20-cm containers, respectively.

*Foliage description.*—Quantity: Usually about two to three per shoot; about 10 to 21 leaves per container. Length: About 10 to 13 cm. Width: About 7 to 9 cm. Shape: Ovate. Apex: Apiculate. Base: Auriculate; lobes not overlapping. Margin: Entire. Texture: Smooth, glabrous, leathery. Color: Young leaves, upper surface: 144A to 144B. Young leaves, lower surface: 144B to 145B. Mature leaves, upper surface: Darker than 137A. Mature leaves, lower surface: 146B to 146C. Petiole: Length: About 12 to 16 cm. Color: Close to 144A, slight anthocyanin, 59A. Geniculum length: About 1.5 cm. Geniculum diameter: About 3 mm. Geniculum color: 144B.

Inflorescence description:

*Inflorescence arrangement.*—Spathes with spadices held beyond the foliage. Flowering structures arise from leaf axils. Freely flowering; continuous flowering year-round; numerous spathes/spadices per plant.

*Inflorescence longevity.*—Spathes/spadices last about six weeks under winter conditions and about three months under summer conditions; persistent.

*Flowers.*—Quantity per spadix: About 80. Shape: Rounded. Diameter: About 1 mm, maximum.

*Spathe.*—Length: About 6 to 7 cm. Width: About 7 to 9 cm. Shape: Broadly cordate. Apex: Apiculate. Base: Straight. Margin: Entire. Texture: Leathery, glabrous, slight blistering, glossy. Color: When opening: 47C to 47D; lobe, green, 144A. Front surface: 47C to 47D; lobes, green, 144A. Back surface: 48D; lobes, green, 144A. After senescence: Center, 43C; green lobal areas increase in area with development, mostly green, 144A, with brownish red flush.

*Spadix.*—Length: About 2 to 3 cm. Diameter: About 5 mm. Shape: Columnar. Cross section: Rounded. Longitudinal axis: Very weakly recurved. Color: Base and mid-section: Close to 47D. Apex: 44D. After senescence: Close to 146C.

*Scape.*—Length: About 20 to 25 cm. Aspect: Strong and erect. Color: 144A, slight anthocyanin, 59A.

*Reproductive organs.*—Androecium: Pollen color: Creamy white, 158D. Gynoecium: Stigma shape: Ovoid. Ovary: Protogyneous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Lady Love', as illustrated and described.

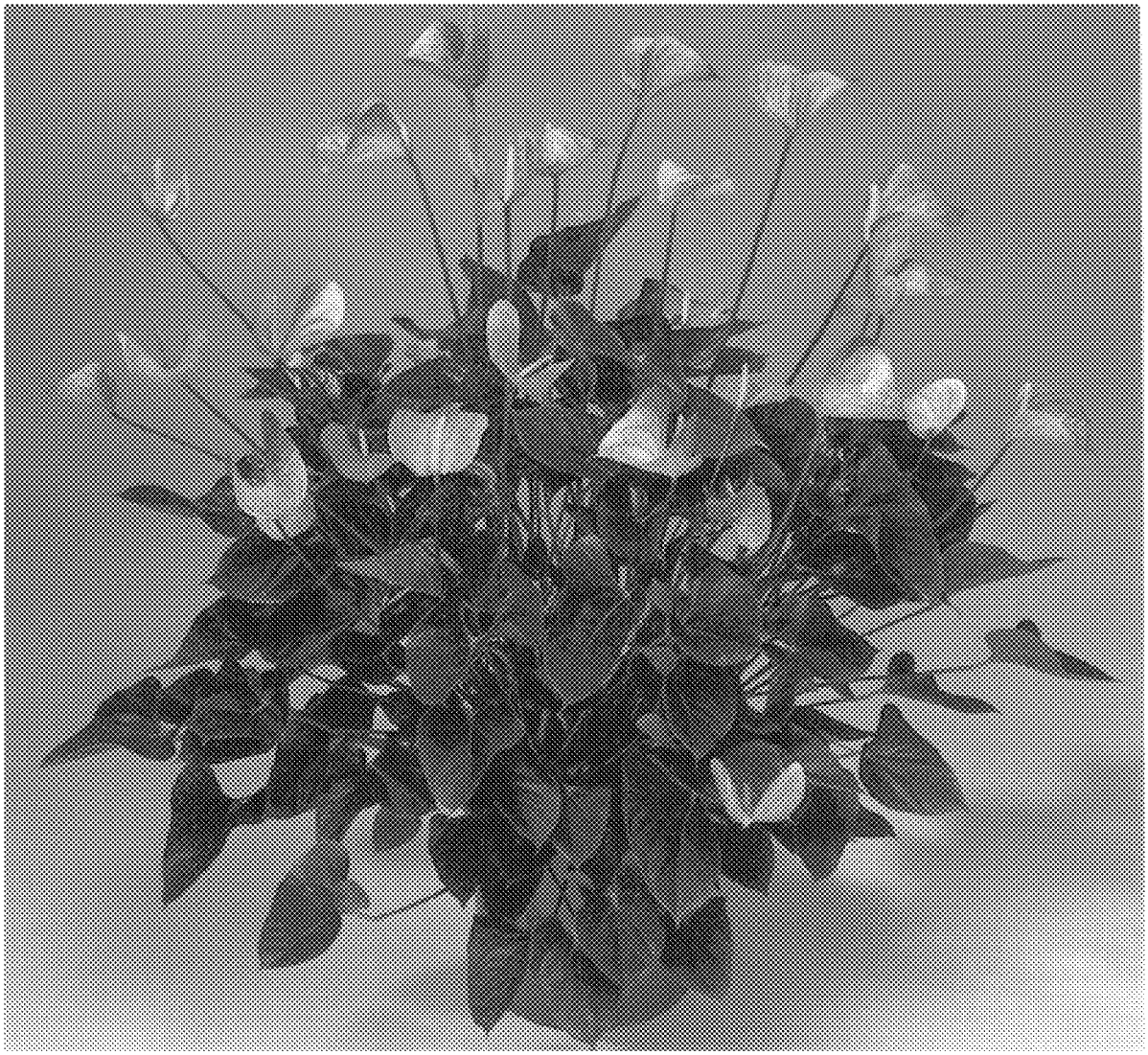

* * * * *